United States Patent
Callahan et al.

[11] Patent Number: 6,083,261
[45] Date of Patent: Jul. 4, 2000

[54] CROSSED HAPTICS FOR INTRAOCULAR LENSES

[76] Inventors: Wayne B. Callahan, P.O. Box 784, Abingdon, Va. 24212-0784; J. Scott Callahan, 1407 Arbor Knoll Blvd., Antioch, Tenn. 37013

[21] Appl. No.: 09/084,989

[22] Filed: May 28, 1998

[51] Int. Cl.[7] .................................................. A61F 2/16
[52] U.S. Cl. ...................... 623/6.38; 623/6.4; 623/6.42; 623/6.43
[58] Field of Search ......................... 623/4, 5, 6, 6.11, 623/6.38, 6.4, 6.42, 6.43

[56] References Cited

U.S. PATENT DOCUMENTS

| | | |
|---|---|---|
| 4,254,509 | 3/1981 | Tennant . |
| 4,573,998 | 3/1986 | Mazzocco . |
| 4,585,456 | 4/1986 | Blackmore . |
| 4,655,775 | 4/1987 | Clasby, III . |
| 4,711,638 | 12/1987 | Lindstrom . |
| 4,769,035 | 9/1988 | Kelman . |
| 4,795,460 | 1/1989 | Anis . |
| 4,804,361 | 2/1989 | Anis . |
| 4,816,032 | 3/1989 | Hetland . |
| 4,842,600 | 6/1989 | Feaster . |
| 4,863,463 | 9/1989 | Tjan . |
| 4,878,911 | 11/1989 | Anis . |
| 4,950,290 | 8/1990 | Kammerling . |
| 4,994,080 | 2/1991 | Shepard . |
| 5,098,444 | 3/1992 | Feaster . |
| 5,108,429 | 4/1992 | Wiley . |
| 5,171,320 | 12/1992 | Nishi . |
| 5,258,025 | 11/1993 | Fedorov et al. . |
| 5,266,074 | 11/1993 | Nishi et al. . |
| 5,366,501 | 11/1994 | Langerman . |
| 5,443,506 | 8/1995 | Garabet . |
| 5,480,428 | 1/1996 | Fedorov et al. . |
| 5,489,302 | 2/1996 | Skottun . |
| 5,522,890 | 6/1996 | Nakajima et al. . |

FOREIGN PATENT DOCUMENTS

| | | |
|---|---|---|
| 2653325 | 4/1991 | France . |
| 2666503 | 3/1992 | France . |
| 2687304 | 8/1993 | France . |
| 3722910 | 1/1989 | Germany . |
| 4030005 | 3/1992 | Germany . |
| 1377086 | 11/1986 | U.S.S.R. . |
| 2124500 | 2/1984 | United Kingdom . |

*Primary Examiner*—Dinh X. Nguyen
*Attorney, Agent, or Firm*—Waddey & Patterson; Edward D. Lanquist, Jr.

[57] ABSTRACT

An intraocular lens with crossed haptics, suitable for implantation in either a phakic or an aphakic eye and a method for implanting and releasing the haptics after implantation in the eye. The lens comprises a very thin, deformable optic having two pairs of haptics attached to the optic by means of two stems 180° apart on the circumference of the optic, each tapering to a tip having one haptic each connected to opposite edges of the stem. Each haptic has a footplate defined at the free end of the haptic. Each haptic sweeps about the periphery of the optic so that the angle subtended by a radial line extending from the center of the optic through the center of a footplate and a second radial line extending from the center of the optic through the center of the stem to which it attaches is about 135°. The lens is symmetrical about an axis extending through the opposing stems, with each haptic crossing either over or under the haptic connected to the opposing stem on the same side of the axis. The lens is inserted into the eye by using a previously prepared seriated suture joined by a viscoelastic material to fold the lens in a tubular shape and compress the haptics, inserting the lens in the eye, centering the lens, dissolving the viscoelastic material with saline solution, and removing the seriated suture by pulling a free end of the suture left outside the eye during insertion. When released, the footplates of the four haptics lie on a circle concentric with the optic, subtending four substantially equal arcs.

18 Claims, 3 Drawing Sheets

CROSSED HAPTICS FOR INTRAOCULAR LENSES

BACKGROUND OF THE INVENTION

1. Field of the Invention

The present invention relates the field of ophthalmology, and particularly to crossed haptics for intraocular lenses ("IOL"), the haptics being suitable for implantation of an appropriate optic in either a phakic or an aphakic eye.

2. Description of the Related Art

Ophthalmologists have been developing the art of implanting an artificial lens in the human eye for many years, both to replace the natural lens which has been removed due to disease (an aphakic eye), and to supplement the natural lens with a corrective lens (a phakic eye).

Various pathologic disease processes can cause deterioration of the natural lens requiring removal of the lens, most notably the opacification of the lens which occurs in cataracts. In the developmental stage, cataracts may be treated by frequent changes of eyeglass prescription. When useful vision is lost, the natural lens is generally removed, either intact or by emulsification. When the lens has been removed, correction is achieved either through spectacles, contact lenses, or an intraocular implant.

Common vision problems include myopia (nearsightedness) hypermetropia (hyperopia or farsightedness) and astigmatism. Traditionally such vision problems have been treated with corrective lenses in spectacles or contact lenses. However, as significant improvements and experience has been gained, the use of intraocular implants using corrective lenses has increased.

Generally, the lens separates the aqueous humor from the vitreous body. The iris separates the region between the cornea or anterior of the eye and the lens into an anterior chamber and a posterior chamber. The lens itself is contained in a membranes known as the capsule or capsular sac. When the lens is removed from the eye, the capsule may also be removed (intracapsular excision), or the anterior portion of the capsule may be removed with the lens leaving the posterior portion of the capsule intact (extracapsular extraction), often leaving small folds or flaps from the anterior portion of the capsule. In an intraocular implant, the artificial or prosthetic lens may be inserted in the anterior chamber, the posterior chamber, or the capsular sac. The artificial lenses are usually fixedly attached within the eye, either by stitching to the iris, or by some supporting means or arms attached to the lens, often in the form of sweeping arms called haptics.

Examples of lens for implantation in the anterior chamber include: U.S. Pat. No. 4,254,509, issued Mar. 10, 1981 to Jerald L. Tennant (an accommodating lens with 2 haptics 180° apart arched posteriorly to optic, with an arc at the end of each haptic defining feet); U.S. Pat. No. 4,816,032, issued Mar. 28, 1989 to Jens G. Hetland (optic with a hole in the center to equalize pressure and prevent glaucoma, having 2 loop haptics); and Soviet Invention Certificate No. SU 1377086, published Nov. 4, 1986 (optic with two pairs of crossed haptics).

An example of a lens for implantation in the posterior chamber is shown in U.S. Pat. No. 5,108,429, issued Apr. 28, 1992 (optic with concentric support ring attached by micromotors controlled by computer to adjust the position of the lens for loss of focal power or astigmatism resulting from the surgery).

A number of advances have dealt with implants in the capsular bag, which attempt to take advantage of the capsular membrane too avoid damage to the tissue of the eye. Among them are: U.S. Pat. No. 4,711,638, issued Dec. 8, 1987 to Richard L. Lindstrom (2 haptics attached to one quadrant of optic, forming semicircles on opposite sides of the optic, and open ended 180° from their point of attachment); U.S. Pat. No. 4,795,460, issued Jan. 3, 1989 to Aziz Y. Anis (2 haptics circumferentially surrounding optic by about 350°, attached to the optic 180° apart); U.S. Pat. No. 4,804,361, issued Feb. 14, 1989, also to Anis (optic surrounded by supporting ring connected to optic by two elongated, curved members); U.S. Pat. No. 4,842,600, issued Jun. 27, 1989 to Fred T. Feaster (a single haptic overlapping itself with a noose at the end for guiding the haptic); U.S. Pat. No. 4,863,463, issued Sep. 5, 1989 to Tik T. Tjan (optic with concentric supporting ring attached by two elongated, curved members); U.S. Pat. No. 4,878,911, issued Nov. 7, 1989 to Aziz Y. Anis (optic with concentric supporting ring connected by 2 straight segments 180° apart); U.S. Pat. No. 5,171,320, issued Dec. 15, 1992 to Okihiro Nishi (optic with grooves on periphery receiving anterior flaps of capsule); U.S. Pat. No. 5,266,074, issued Nov. 30, 1993 to Nishi, et al. (same as above, but with different shapes for periphery); U.S. Pat. No. 5,366,501, issued Nov. 22, 1994 to David W. Langerman (optic with two concentric support rings attached by straight bars, the outer ring angled anteriorly); U.S. Pat. No. 4,655,775, issued Apr. 7, 1987 to Thomas J. Clasby III (optic with ridges to offset optic from posterior surface of posterior chamber, having 2 bent haptics); and U.S. Pat. No. 4,950,290, issued Aug. 21, 1990 to William Kammerling (lens to reduce posterior capsular opacification, having biconvex optic with helically shaped loop haptic sloping 10° anterior to the optic).

Examples of correcting lenses are described in U.S. Pat. No. 4,585,456, issued Apr. 29, 1986 to John M. Blackmore (corrective lens in contact with natural lens, having 2 appendages or haptics fitting into the ciliary sulcus); U.S. Pat. No. 4,769,035, issued Sep. 6, 1988 to Charles D. Kelman (corrective lens with folding optic and two broad haptics 180° apart, each having an arc at the free end to define feet, the optic being folded and inserted in the posterior chamber through the pupil); U.S. Pat. No. 5,098,444, issued Mar. 24, 1992 to Fred T. Feaster (optic glued to anterior surface of natural lens); U.S. Pat. No. 5,258,025, issued Nov. 2, 1993 to Fedorov, et al. (optic with same radius of curvature as natural lens, two broad haptics having feet fitting in Zinn's zonules); U.S. Pat. No. 5,480,428, issued Jan. 2, 1996, also to Fedorov, et al. (corrective lens floating in the eye); and our own pending application (a deformable intraocular corrective lens with 2 curved haptic 180° apart).

Examples of accommodating lenses are shown in U.S. Pat. No. 5,443,506, issued Aug. 22, 1995 to Antoine L. Garabet (varying the power of the lens by a fluid loop through a first optic, the fluids having differing refractive indices and responding to electrical impulses from the ciliary body); U.S. Pat. No. 5,489,302, issued Feb. 6, 1996 to Bernt C. Skottun (lens with fluid and membranes responding to change in pressure caused by ciliary muscle, changing volume of fluid and refractive index of lens).

U.S. Pat. No. 4,573,998, issued Mar. 4, 1986 to Thomas P. Mazzocco, describes various arrangements of haptics, none of which are crossed, and various methods for implanting deformable intraocular lenses, none of which describe using a viscoelastic material to join seriated sutures. U.S. Pat. No. 4,994,080, issued Feb. 19, 1991 to Dennis P. Shepard, shows an optic with at least one opening to improve focusing for depth, with embodiments having either 2 or 4 haptics, none being crossed. U.S. Pat. No. 5,522,890, issued Jun. 4, 1996 to Nakajima, et al., discloses a deformable lens having two haptics attached to the optic using right angled reinforcements at the periphery of the optic which are thicker than the periphery, the lens being folded into a tube shape for implantation in the eye.

Some foreign patents showing slightly different arrangements of the haptics include: U.K. Patent. No. 2,124,500, published Feb. 22, 1984 (annular ring attached to optic by fibers); German Patent No. 3,722,910, published Jan. 19, 1989 (two haptics, each having a substantially quarter moon shape); French Patent No. 2,653,325, published Apr. 26, 1991 (an annular haptic bound to haptic by a bridge, and 180° away by a convex loop); French Patent No. 2,666,503, published Mar. 13, 1992 (two haptics joining optic on the same side, extending in semicircle on opposite side of optic, and having a stop to prevent crossing of haptics); German Patent No. 4,030,005, published Mar. 26, 1992 (two haptics spreading out from a common bridge to optic); and French Patent No. 2,687,304 published Aug. 20, 1993 (optic with annular support ring joined to optic by two bridges).

Despite the advances, there remain problems with intraocular implants which may be ameliorated by the improved haptics and method of releasing the haptics of the present invention inside the bulb of the eye. When an intraocular lens is inserted in the eye, an incision is made in the cornea or sclera. The incision causes the cornea to vary in thickness, leading to an uneven surface which causes astigmatism. The insertion of a rigid lens through the incision, even with compressible haptics, requires an incision large enough to accommodate the rigid lens (at least 6 mm), and carries with it the increased risk of complications, such as infection, laceration of the ocular tissues, and retinal detachment. Deformable intraocular lenses made from polymethylmethacrylate ("PMMA"), polysulfone, silicone or hydrogel may be inserted through a smaller incision, about 4 mm.

Nevertheless, it is critical that the lens be properly centered and properly fixed so that it does not slip out of position. In an anterior chamber implant, the lens should be positioned between the cornea and the iris, but avoiding contact with either to prevent corneal damage, proliferation of corneal epithelium on the anterior surface of the lens causing opacification, or iritis. If the lens is not positioned properly with respect to the pupil, too much light may be admitted to the retina, causing serious vision difficulties. The haptics or lens support generally lodge in the angle of the anterior chamber, but it is desirable that the haptics be as flexible as possible while keeping the area of surface contact between the haptic and the eye tissue as small as possible to avoid swelling, laceration, infection, or other damage to the eye tissue.

The anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The lens must be positioned so the flow of fluid is not blocked or glaucoma may result. If the haptics fit slightly too tight, the patient experiences pain and the lens may have to be removed. If the haptics are slightly too loose, the lens may move into the endothelial cells on the inside of the cornea causing permanent loss of vision.

Posterior chamber and capsular bag implants involve both similar and different considerations. In posterior chamber implants, the haptics normally lodge in the ciliary sulcus, entailing the same considerations with regard to tissue swelling and damage through laceration. Most posterior chamber implants are placed in the posterior capsule in order to take advantage of the insulating properties of the capsule membrane. Here, it is desirable to stretch the capsule as much as possible, vaulting the optic posteriorly to avoid having the anterior flaps proliferate and opacify the anterior surface of the lens, and to stretch the capsule taut. The corrective lens for the phakic eye must be extremely thin in order to fit into the limited space in either the anterior or posterior chambers with the natural lens still in place, but must have some area of thickness at the periphery of the lens to support attachment of the haptics.

Regardless of the type of implant, some means of centering the implant is essential. Currently artificial lenses are implanted using special tools to compress the haptics, such as forceps or cannulas, or rely on microhooks to manipulate the optic through a hole in the surface of the optic. Haptics designed to center in the eye and means for compressing the haptics without the use of bulky tools during centering is therefore desirable.

The present invention solves these problems by a deformable intraocular lens having two pairs of crossed haptics with footplates connected to the optic by a stem. The lens is inserted into the eye using a unique method of compressing the haptics by seriated sutures temporarily joined using a viscoelastic material, which is dissolved after centering the lens in the eye.

Although the Soviet Invention Certificate SU 1,377,086 also shows crossed haptics, it is noted that (1) the optic is rigid, requiring a longer incision (6 mm) and the increased risk of complications during insertion, as well as restricting use to anterior chamber implants; (2) the haptics do not have footplates, placing more surface area of the haptic in contact with the eye tissue; (3) there is no stem between adjacent haptics, but rather each haptic is individually attached to the haptic, requiring the periphery of the lens to be thick enough for attachment of the haptics; and (4) the haptics extend outwardly from the optic for ¾ of their length before turning concavely towards the lens, virtually precluding compressing the haptics either in front of or behind the lens, presenting a longer profile for insertion through the incision.

Thus, none of the above inventions and patents, taken either singularly or in combination, is seen to describe the instant invention as claimed. Hence the crossed haptics for intraocular lenses solving the aforementioned problems is desired.

SUMMARY OF THE INVENTION

The present invention comprises crossed haptics attached to an intraocular lens suitable for implantation in either a phakic or an aphakic eye and a method for implanting and releasing the haptics after implantation in the eye. The lens comprises a very thin, deformable optic having two pairs of haptics attached to the optic by means of two stems 180° apart on the circumference of the optic, the stems being wider and thinner at the base attached to the periphery of the optic, and tapering to a narrower and thicker tip to which each haptic is connected at opposite edges of the stem. Each haptic has a footplate defined at the free end of the haptic. Each haptic sweeps about the periphery of the optic so that the angle subtended by a radial line extending from the center of the optic through the center of a footplate and a second radial line extending from the center of the optic through the center of the stem to which it attaches is about 135°. The lens is symmetrical about an axis extending through the opposing stems, with each haptic crossing either over or under the haptic connected to the opposing stem on the same side of the axis. The lens is inserted into the eye by using a previously prepared seriated suture joined by a viscoelastic material to fold the lens in a tubular shape and compress the haptics, inserting the lens in the eye, centering the lens, dissolving the viscoelastic material with saline solution, and removing the seriated suture by pulling a free end of the suture left outside the eye during insertion. When released, the footplates of the four haptics lie on the circumference of a circle concentric with the optic, subtending four substantially equal arcs.

Accordingly, it is a principal object of the invention to provide crossed haptics for intraocular lenses suitable for implantation into either a phakic or an aphakic eye which may be centered in the eye easily in the form of a deformable lens having crossed haptics with footplates at their free ends which may be inserted in the eye using seriated sutures temporarily joined by a viscoelastic material to compress the lens and haptics in a tubular shape, dissolving the viscoelastic material and removing the suture after centering the lens.

It is another object of the invention to provide crossed haptics for intraocular lenses suitable for implantation into either a phakic or an aphakic eye which may be centered in the eye easily in the form of a deformable lens having two pairs of crossed haptics with footplates wherein the position of the lens is fixed in the eye by four foot plates lying on the circumference of a circle concentric with the optic and subtending substantially equal arcs.

It is a further object of the invention to provide crossed haptics for intraocular lenses suitable for implantation into either a phakic or an aphakic eye in which damage to the tissue of the eye is reduced by minimizing haptic contact with the eye to four footplates sized and shaped to exert a minimum of pressure on the tissues of the eye.

Still another object of the invention is to provide crossed haptics for intraocular lenses suitable for implantation into either a phakic or an aphakic eye having two pairs of crossed haptics attached to the optic by a pair of stems in which the lens may be implanted in the anterior chamber, the posterior chamber, or the capsular sac, depending on the conformation of the lens.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates to crossed haptics for intraocular lenses and a method for inserting the lens into the bulb of the eye and releasing the haptics. Haptics are spring-like structures which support the optic of an intraocular lens implant in order to maintain the lens in a relatively fixed position within the eye.

Figure 1:
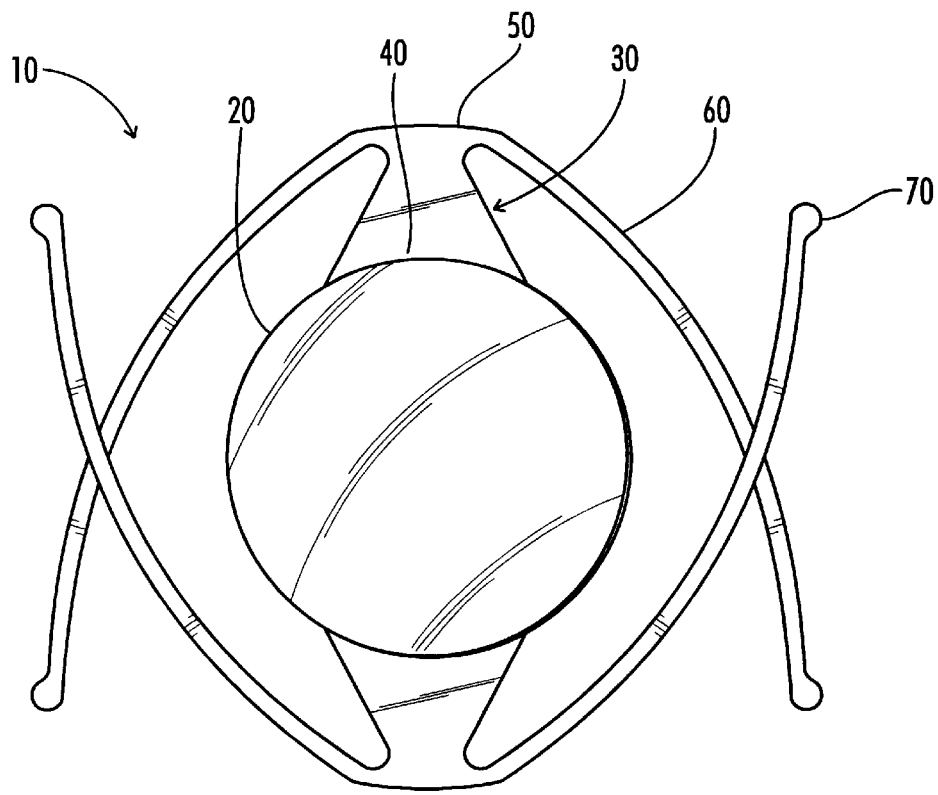
FIG. 1 is an front elevational view of crossed haptics for intraocular lenses according to the present invention.

FIG. 1 shows an intraocular lens, designated generally as reference 10 in the Figures, showing exemplary crossed haptics 60 according to the present invention. The lens comprises a central optical portion referred to as the optic 20. The optic 20 is designed to replace the natural lens in an aphakic eye, or to supplement and correct defects in the natural lens in a phakic eye. The optic 20 will generally be constructed in varying thicknesses, shapes (generally disk shaped, with its outer surfaces biconvex, plano-convex, etc.), and focal powers or properties according to the application. The crossed haptics 60 of the present invention are designed to be used with optics 20 having different optical properties. However, they are intended for use with and are integral with deformable optics 20 made from polymethylmethacrylate ("PMMA"), polysulfone, silicone or hydrogel, preferably PMMA, and are capable of being deformed by compressing, rolling folding, stretching, etc. for insertion into the eye through a small incision, but being somewhat resilient and having memory characteristics to revert to their original shape when the force producing deformation is removed. In the preferred embodiment, the optic 20 is about 6 mm in diameter and the edge of the optic is about 0.050 mm thick.

A pair of substantially flat stems, designated generally as 30, extend from the edges of optic 20, each stem having a line of symmetry separated from the other by approximately 180°. The base 40 of the stem 30 is wide and thin where it attaches to the edge of the optic 20, being about 3 mm wide and 0.05 mm thick. As it extends radially from optic 20, the stem 30 becomes progressively narrower and thicker, being about 1 mm wide and 0.127 mm thick at the tip 50 or free end of the stem 30.

Each stem 30 has a pair of haptic arms 60 attached to opposite edges of the stem 30 near the tip 50. The width of the stem 30 at its base 40 and the thickness of the stem 30 at its tip 50 provide strength and a secure anchor for mounting the haptic 60 arms to the optic 20, while retaining a sufficiently flexible stem 30 to manipulate the haptics 60 as set forth below.

Each of the haptic arms 60 has a footplate 70 at its free end. The footplates 70 are small, rounded protrusions at the end of the haptics 60 extending slightly laterally from the outer edge of the haptic 60. The haptic arms 60 are arcuately shaped and extend from opposite sides of the tip 50 of the stem 30, being concave relative to the edge of the optic 20. Along a radial line extending from the center of the optic 20, the tip of the stem is about 4.75 mm from the center of the optic 20 and the outer edge of each footplate 70 rests in a circle about 7 mm from the center of the optic 20. Each haptic 60 sweeps about the periphery of the optic 20 so that the angle subtended by a radial line extending from the center of the optic 20 through the center of a footplate 70 and a second radial line extending from the center of the optic 20 through the center of the stem 30 to which it attaches is about 135°. The lens 10 is symmetrical about an axis extending through the opposing stems 30, with each haptic 60 crossing either over or under the haptic 60 connected to the opposing stem 30 on the same side of the axis.

Figure 2:
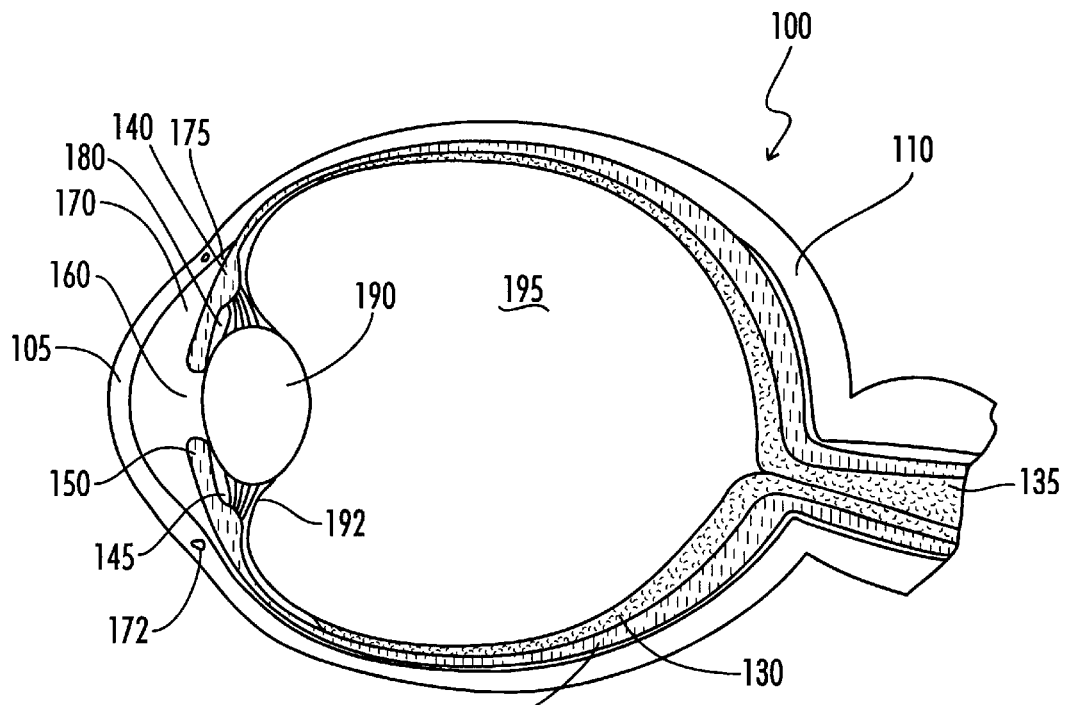
FIG. 2 is a horizontal section of the human eye.
Figure 4:
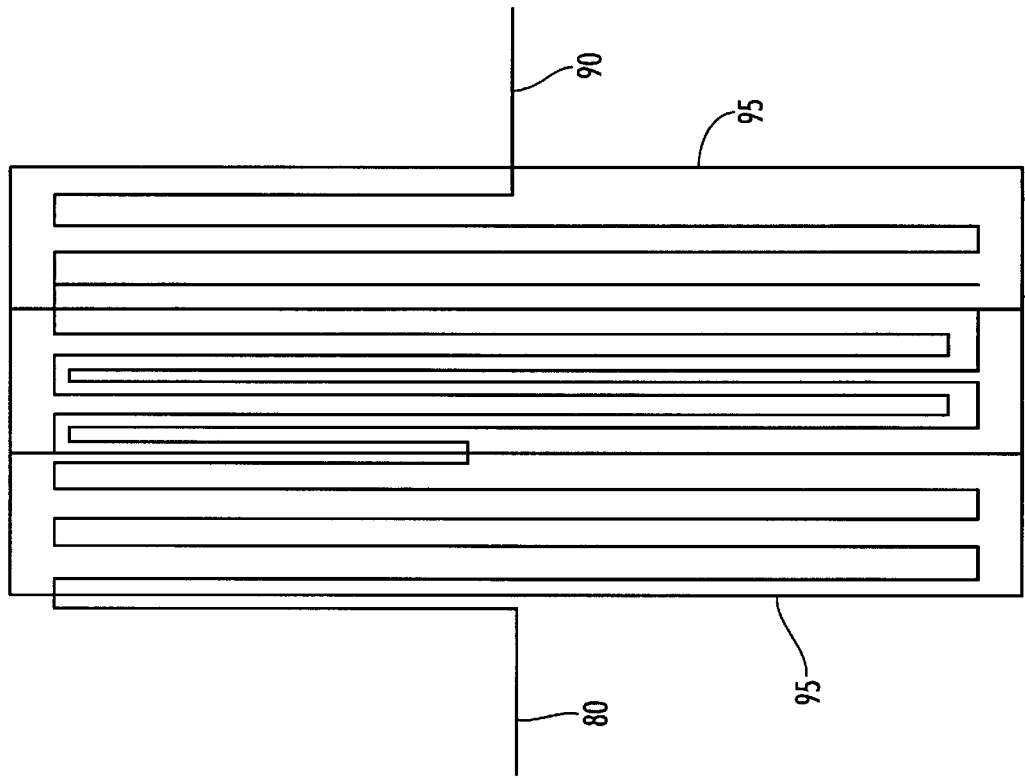
FIG. 4 is a plan view showing the preparation of suture material used to insert the lens of the present invention into the eye.

FIG. 2 is a horizontal section of the bulb of the human eye 100. The eye 100 is coated by three tunics: an outer layer composed of a thick sheath called the sclera 110 covering the posterior ⅚ of the eye, and a transparent covering called the cornea 105 over the anterior ⅙; a middle layer called the choroid 120 posteriorly, containing the vasculature and musculature of the eye, joining the ciliary body 140 and iris 150 anteriorly; and an inner layer called the retina 130, comprising a nervous membrane. The tunics are pierced posteriorly by the optic nerve 135 and blood vessels of the retina. The iris 150 is an opaque diaphragm having an aperture called the pupil 160 at its center, and expands or contracts the opening of the pupil 160 by contracture and. relaxation of the ciliary muscle in the ciliary body 140 to regulate the flow of light into the eye 100. The natural crystalline lens 190 is suspended between the iris 150 anteriorly and the vitreous body 195 posteriorly by ligaments known as this zonules of Zinn 192 attached to the muscles of the eye 100 in the ciliary body 140. At the junction between the iris 150 and the ciliary body 140 is a shallow depression known as the ciliary sulcus 145. The iris 150 and pupil 160 divide the anterior region of the eye 100 into the anterior chamber 170 and the posterior chamber 180, which are filled with the aqueous humor, a fluid secreted by the ciliary process and flowing from the posterior chamber 180 through the pupil 160 into the anterior chamber 170. At the angle 175 of the anterior chamber 170 (at the junction of the cornea 105, and the iris 150), the fluid is filtered through the spaces of Fontana and the pectinate villi and drains through the sinus venosus sclerae, or canals of Schlemm 172. The lens 190 is contained within a thin membrane called the lens capsule (not shown).

Figure 7:
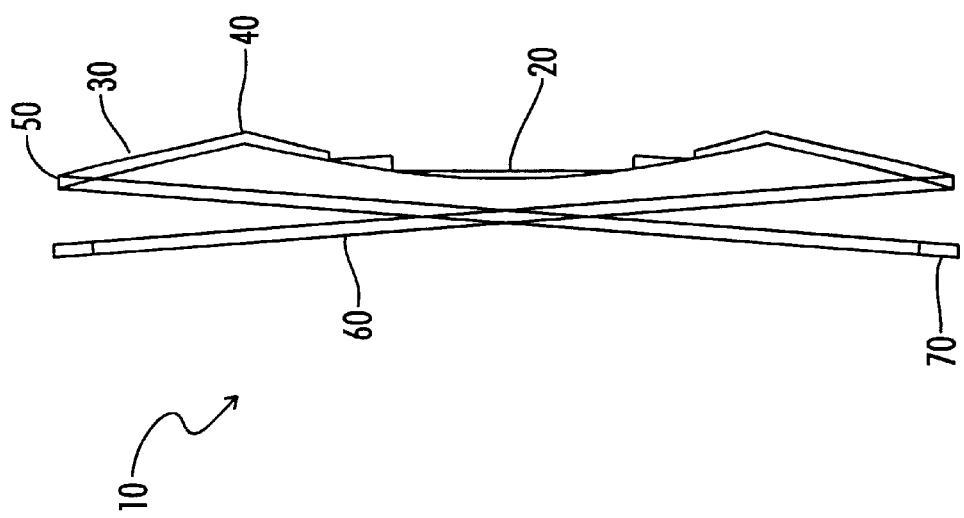
FIG. 7 is a plan view of a third embodiment of an intraocular lens with crossed haptics according to the present invention adapted for insertion into the posterior chamber of a phakic eye.
Figure 6:
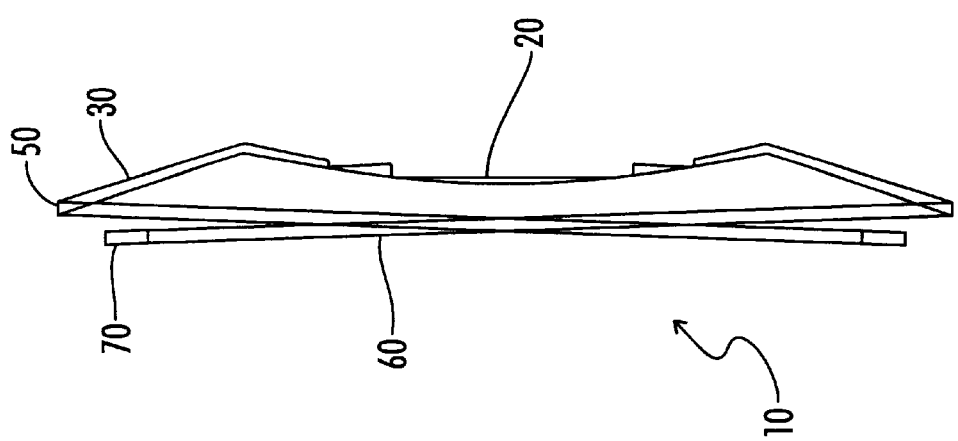
FIG. 6 is a plan view of a second embodiment of an intraocular lens with crossed haptics according to the present invention adapted for insertion into the posterior chamber of an aphakic eye.
Figure 5:
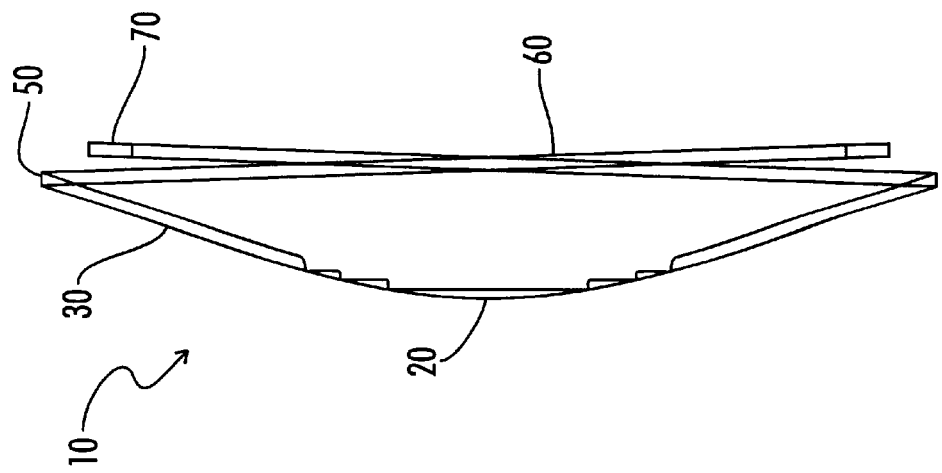
FIG. 5 is a plan view of a first embodiment of an intraocular lens with crossed haptics according to the present invention adapted for insertion into the anterior chamber of an aphakic eye.

The crossed haptics 60 of the present invention may be used for implants into the anterior chamber 170, the posterior chamber 180, or the posterior portion of the lens 190 capsule. FIG. 5 shows the conformation of the IOL 10 for implantation in the anterior chamber 170 of an aphakic eye. As shown in the plan view, the optic 20 is in an anterior plane, and the stems 30 are angled posteriorly so that the optic 20 is vaulted anteriorly, with the footplates 70 occupying a plane posterior to the tips 50 of the stems 30. FIG. 6 shows the conformation of the IOL 10 for implantation in the posterior chamber 180 of an aphakic eye. As; shown in the plan view, the optic 20 is in a posterior plane, and the stems 30 are angled posteriorly so that the optic 20 is vaulted posteriorly, with the footplates 70 occupying a plane anterior to the tips 50 of the stems 30. FIG. 7 shows the conformation of the IOL 10 for implantation in the posterior chamber 180 of a phakic eye. As shown in the plan view, the optic 20 is in a posterior plane, and the stems 30 are angled posteriorly so that the optic 20 is vaulted posteriorly, with the footplates 70 occupying a plane anterior to the tips 50 of the stems 30.

It will be appreciated that in each of the three conformations shown above, the optic 20, the tip 50 of the stem 30, and the footplates 70 of the haptics 60 each occupy a different frontal or coronal plane, with the tip 50 of the stem 30 always occupying the middle plane. When the haptics 60 are released, the footplates 70 occupy positions superior, inferior, and lateral to the stems 30. As a consequence of this geometry, the stems 30 do not come into contact with the tissue of the eye 100, and are prevented from lacerating or damaging the tissues.

It will also be appreciated that when the haptics 60 are released in the eye 100, the haptics 60 expand so that, in the average human eye 100, the footplates 70 rest on the circumference of a circle concentric with the optic 20 and subtend four substantially equal arcs of 90° each about the circumference of the circle. The footplates 70 are so sized and shaped that surface contact with and pressure applied to the tissues of the eye 100 are kept to a minimum to avoid complications due to swelling, lacerations or other damage to the eye tissue. For phakic eyes, a corrective IOL may be implanted with the lens 10 centered in the anterior chamber 170, the footplates normally resting in the angle 175 of the anterior chamber 170, or in the posterior chamber 180 between the iris 150 and the natural lens 190, the footplates 70 normally resting in the ciliary sulcus 145. For aphakic eyes, the IOL 10 may be implanted in the anterior chamber 170 with the footplates 70 normally resting in the angle 175 of the anterior chamber 170, or in the posterior chamber 180 with the footplates 70 normally resting in the ciliary sulcus 145, or in the capsular bag with the footplates 70 within and stretching the posterior portion of the capsule of the lens 190.

Figure 3:
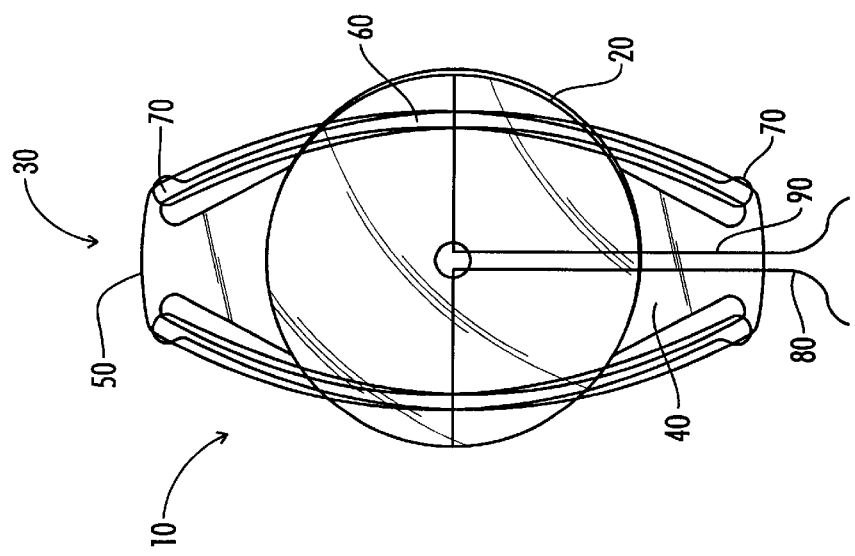
FIG. 3 is a view of crossed haptics for intraocular lenses according to the present invention with the lens and haptics compressed for insertion into the eye.

A method for implanting the haptics 60 and releasing the haptics 60 after implantation in the eye 100 can now be described. A piece of suture material is cut into a first piece 80 and a second piece 90 which are seriated as shown in FIG. 3. The two pieces of suture material are sequenced with a pair of outer zones 95, each with a single thread arranged in substantially S-shaped loops, and a center zone 85 between the two outer zones 95, in which the first piece and the second piece have overlapping lengths with the S-shaped loops paralleling each other. The suture material is coated with a viscoelastic material which is unreactive to and harmless to the eye 100, preferably a heavy layer or paste of chondroitin sulfate, and allowed to dry. The center zone 85 may receive a second coat of the viscoelastic material to ensure that the center zone 85 has a thicker layer of the viscoelastic material than the outer zones 95 and that the first piece 80 is temporarily bonded to the second piece 90.

After the viscoelastic material has dried, the seriated suture material is tied around the lens 10 until the optic 20 is deformed into a tube and the haptics 60 are compressed and tucked either anteriorly or posteriorly to the optic 20, as shown in FIG. 3. The surgeon inserts the lens 10 into a minimal incision in the cornea 105 or sclera 110 and positions the lens 10 in the eye 100, leaving a loose end of first piece 80 and second piece 90 outside the eye. After positioning the lens 10, the surgeon inspirates an irrigating solution, preferably saline solution, onto the viscoelastic paste, which dissolves the paste. Since the outer zones 95 have a thinner layer of paste, the outer zones 95 tend to dissolve before the center zone 85. As the paste dissolves, the S-shaped loops of the outer zones tend to unwind and lengthen, releasing the haptic 60 arms, which spring back to their original conformation due to the memory characteristics of the lens 10 material, the surgeon tweaking the position of the lens 10 by manipulating the haptics as they unwind, if necessary. By the time the outer zones 95 are free of the viscoelastic paste, the outer edges of the footplates 70 rest against the tissue of the eye 100 in a circular pattern. The size of the circle depends on the size of the eye 100. Typically the human eye 100 is 11.5 to 13.5 mm in diameter.

Additional irrigating solution is inspirated to the center zone 85 until all the paste is dissolved, separating the first piece 80 of suture material from the second piece 90. The suture material can then be removed from the eye 100 by gently pulling the loose end of first piece 80 or second piece 90.

Thus, the crossed haptics 60 of the present invention and the method of inserting and releasing the haptics 60 present a means for supporting an IOL 10 which offers improved centering of the lens 10 while minimizing damage to the tissue of the eye 100.

It is to be understood that the present invention is not limited to the embodiments described above, but encompasses any and all embodiments within the scope of the following claims.

We claim:

1. Intraocular lenses with cross haptics for implantation in the human eye, comprising:
    a) a lens optic, the optic being substantially disc shaped;
    b) a pair of substantially flat stems, each stem having a base end attached to the edge of said optic diametrically opposite the other stem, and a tip end extending radially from said optic, the stems being wide and thin at the base and being progressively narrower and thicker from the base end to the tip end;
    c) a pair of arcuate haptic arms attached to each stem, each haptic arm having a small rounded footplate at its end, each haptic arm extending from opposite sides of the tip of said stem and sweeping around the periphery of said optic, being concave relative to the edge of said optic; and wherein
    d) each haptic arm crosses the haptic arm attached to the diametrically opposite stem on the same side of an axis running through the center of said diametrically opposite stems;
    e) said intraocular lens is made from a resilient, deformable material, whereby said lens regains its shape after being compressed, bent, folded or stretched.

2. The intraocular lenses with cross haptics according to claim 1, wherein the footplates of said haptic arms slightly protrude lateral to the outside edge of said haptic arms, whereby the surface area of said haptic arms in contact with and the pressure applied to the tissue of the eye is minimized.

3. The intraocular lenses with crossed haptics according to claim 1, wherein the outer edges of the footplates of said haptic arms lie on the circumference of a circle concentric with said optic and subtend four substantially equal arcs of about 90° about the circumference of the circle when said lens is implanted in the eye.

4. The intraocular lenses with crossed haptics according to claim 1, wherein said optic, the tip of said stem, and the footplates of said haptic arms rest in different coronal planes, the plane containing the tip of the stem lying in the middle of the three planes, and wherein said footplates rest superiorly and inferiorly to the tips of said stems, whereby said stems are prevented from contacting the tissues of the eye.

5. The intraocular lenses with crossed haptics according to claim 1, wherein said optic is vaulted anteriorly, said stems being angled posteriorly, and the footplates of said haptic arms being posterior to the tips of said stems, whereby said lens is adapted for implantation in the anterior chamber of an aphakic eye.

6. The introcular lenses with crossed haptics according to claim 1, wherein said optic is vaulted posteriorly, said stems being angled anteriorly, and the footplates of said haptic arms being anterior to the tips of said stems, whereby said lens is adapted for implantation in the posterior chamber of an aphakic eye.

7. The intraocular lenses with crossed haptics according to claim 1, wherein said lens optic is a corrective lens and wherein said optic is vaulted anteriorly, said stems being angled posteriorly, and the footplates of said haptic arms being posterior to the tips of said stems, whereby said lens is adapted for implantation in the anterior chamber of a phakic eye.

8. The intraocular lenses with crossed haptics according to claim 1, wherein said lens optic is a corrective lens and wherein said optic is vaulted posteriorly, said stems being angled anteriorly, and the footplates of said haptic arms being anterior to the tips of said stems, whereby said lens is adapted for implantation in the posterior chamber of a phakic eye.

9. The method of implanting the intraocular lenses with crossed haptics according to claim 1 in the human eye and releasing the crossed haptics after implantation, comprising the steps of:
    a) cutting suture material into a first piece and a second piece;
    b) arranging said first piece and said second piece in a. series of S-shaped loops having a pair of outer zones, each with a single piece, and a center zone in which the S-shaped. loops of said first piece and said second piece overlap and are substantially parallel;
    c) seriating said first piece and said second piece by coating said outer zones and said center zone with a least one coat of a viscoelastic material, whereby said first piece and said second piece are temporarily bonded to each other;
    d) tying said seriated suture material around said lens, said optic being folded into a tube and said haptic arms being compressed and tucked either anteriorly or posteriorly to said optic;
    e) inserting said lens into the eye through a small incision in the eye, leaving the loose ends of the seriated suture material outside the eye;
    f) centering the lens in the eye;
    g) irrigating the viscoelastic material on the seriated suture material with an irrigating solution, whereby the viscoelastic material dissolves and releases said haptic arms from their compressed position;
    h) continuing to irrigate the viscoelastic material on. the seriated suture material until all of the viscoelastic material dissolves and said first piece separates from said second piece; and
    i) removing said first piece and said second piece of suture material from the eye by gently pulling on the loose end of said first piece and said second piece.

10. The method of implanting according to claim 9, wherein the viscoelastic material comprise chondroitin sulfate.

11. The method of implanting according to claim 9, wherein the irrigating solution is saline solution.

12. The intraocular lenses with cross haptics for intraocular lenses for implantation in the human eye, comprising:
    a) a lens optic;
    b) at least two stems, each stem having a base end attached to the edge of said optic and a tip end extending from said optic; and
    c) an arcuate haptic arm attached to each stem, each haptic arm having a footplate at its end, each haptic arm extending from the tip of said stem and sweeping around the periphery of said optic, being concave relative to the edge of said optic; and wherein d) said intraocular lens is made from a resilient, deformable material, whereby said lens regains its shape after being compressed, bent, folded or stretched.

13. The intraocular lenses with crossed haptics according to claim 12, wherein the outer edges of the footplates of said haptic arms lie on the circumference of a circle concentric with said optic and subtend substantially equal arcs about the circumference of the circle when said lens is implanted in the eye.

14. The intraocular lenses with crossed haptics according to claim 12, wherein said optic, the tip of said stem, and the footplates of said haptic arms rest in different coronal planes, the plane containing the tip of the stem lying in the middle of the three planes, and wherein said footplates rest superiorly and inferiorly to the tips of said stems, whereby said stems are prevented from contacting the tissues of the eye.

15. The intraocular lenses with crossed haptics according to claim 12, wherein said optic is vaulted anteriorly, said stems being angled posteriorly, and the footplates of said haptic arms being posterior to the tips of said stems, whereby said lens is adapted for implantation in the anterior chamber of an aphakic eye.

16. The intraocular lenses with crossed haptics according to claim 12, wherein said optic is vaulted posteriorly, said stems being angled anteriorly, and the footplates of said haptic arms being anterior to the tips of said stems, whereby said lens is adapted for implantation in the posterior chamber of an aphakic eye.

17. The intraocular lenses with crossed haptics according to claim 12, wherein said lens optic is a corrective lens and wherein said optic is vaulted anteriorly, said stems being angled posteriorly, and the footplates of said haptic arms being posterior to the tips of said stems, whereby said lens is adapted for implantation in the anterior chamber of a phakic eye.

18. The intraocular lenses with crossed haptics according to claim 12, wherein said lens optic is a corrective lens and wherein said optic is vaulted posteriorly, said stems being angled anteriorly, and the footplates of said haptic arms being anterior to the tips of said stems, whereby said lens is adapted for implantation in the posterior chamber of a phakic eye.

* * * * *